United States Patent [19]

Pauly et al.

[11] Patent Number: 5,610,026
[45] Date of Patent: Mar. 11, 1997

[54] AGENT FOR THE DETERMINATION OF PEROXIDASE ACTIVITY, A PROCESS FOR ITS PREPARATION AND ITS USE

[75] Inventors: Hans E. Pauly, Dautphetal; Herbert Schwarz, Ebsdorfergrund, both of Germany

[73] Assignee: Behringwerke Aktiengesellschaft, Marburg, Germany

[21] Appl. No.: 291,059

[22] Filed: Aug. 8, 1994

Related U.S. Application Data

[63] Continuation of Ser. No. 817,955, Jan. 8, 1992, abandoned, which is a continuation of Ser. No. 935,333, Nov. 26, 1986, abandoned.

[30] Foreign Application Priority Data

Nov. 28, 1985 [DE] Germany .......................... 35 41 978.4

[51] Int. Cl.$^6$ .............................. C12Q 1/28; C12Q 1/26; C12Q 1/00; C12Q 1/32
[52] U.S. Cl. ................................. 435/28; 435/25; 435/4; 435/26; 435/18; 435/14; 436/63; 436/74; 436/34; 436/507
[58] Field of Search .................................. 435/28, 25, 4, 435/188, 26, 18, 13, 14; 436/63, 74, 34, 507

[56] References Cited

U.S. PATENT DOCUMENTS

| | | | |
|---|---|---|---|
| 4,063,894 | 12/1977 | Ogawa et al. ............................. | 436/66 |
| 4,077,772 | 3/1978 | Geissler et al. ........................... | 435/26 |
| 4,200,508 | 4/1980 | Hirai ........................................ | 435/26 |
| 4,340,394 | 7/1982 | Magers et al. ............................ | 435/26 |
| 4,503,143 | 3/1985 | Gerber et al. .............................. | 435/7 |
| 4,504,579 | 3/1985 | Sun ........................................... | 435/28 |
| 4,891,314 | 1/1990 | Pauly et al. ............................... | 435/28 |
| 5,206,150 | 4/1993 | Tai ............................................ | 435/28 |

FOREIGN PATENT DOCUMENTS 0121317  10/1984  European Pat. Off. .......... C12Q 1/28

OTHER PUBLICATIONS

Andrews et al, Analytical Biochem, vol. 127, pp. 346–350, (1982).
Stedman's Medical Dictionary; 24$^{th}$ Edition; pp. 452, 582, 1048 and 1457.
ByK–Mallinckrodt Chemische Produkte G.m.b.H; Chemical Abstracts; 102(23): 200318W.
Cook, A. H., et al, "Thiazolidines" in *The Chemistry of Penicillin*. (Ed. Clarke) pp. 921–972. (1949).
Pütter et al, "Peroxidases" in *Methods of Enzymatic Analysis*. Third Ed. (Ed. Bergmeyer) pp. 286–293. (1985).
"Methods of Enzymatic Analysis," H. U. Bergmeyer, Ed., 3rd Ed., vol. 1, pp. 210–221, Verlag Chemie, Weinheim (1983).
Holland et al. Tetrahedron, vol. 30, pp. 3299–3302, (1976).
Garner et al. Cancer Letters, 1, pp. 39–42, (1975).
Garner et al. Journal of Forensic Sciences, 21, pp. 816–821, (1976).
Liem et al., Analytical Biochemistry, 98, pp. 388–393, (1979).
Nakane und Kawaoi, "Journal of Histochemistry and Cytochemistry", vol. 22, No. 12, pp. 1084–1091, (1974).
Voller et al., Bull. of the World Health–Organization, vol. 53, pp. 55–65, (1976).

*Primary Examiner*—John Kight
*Assistant Examiner*—Louise Leary
*Attorney, Agent, or Firm*—Finnegan, Henderson, Farabow, Garrett & Dunner, L.L.P.

[57] ABSTRACT

An agent for the detection of peroxidase or of pseudoperoxidase activity, and its preparation and its use are described. The agent contains a tetraalkylbenzidine, a peroxide and buffer substances. The agent according to the invention has, as a peroxidase substrate, the advantage over previous tetraalkylbenzidine-containing substrates that it generates higher color signals.

8 Claims, No Drawings

AGENT FOR THE DETERMINATION OF PEROXIDASE ACTIVITY, A PROCESS FOR ITS PREPARATION AND ITS USE

This application is a continuation, of application Ser. No. 07/817,955, filed Jan. 8, 1992, now abandoned, which is a continuation of application Ser. No. 06/935,333, filed Nov. 26, 1986, now abandoned.

The present invention relates to an agent for the determination of peroxidase activity by a color reaction, and to a process for its preparation and its use.

An essential prerequisite for the introduction of enzyme immunoassays which are equivalent, in respect of their detection sensitivity, to radioimmunological methods has been the availability of stable marker enzymes and corresponding highly sensitive color-forming reagents with which it was possible to register the catalytic activity of these marker enzymes by use of a straightforward measuring technique. Marker enzymes which have proven particularly suitable for this are the oxidoreductases glucose oxidase and peroxidase. In genral peroxidase reactions are among the most frequently used enzymatic detection reactions. For example, all the methods described in "Methods of Enzymatic Analysis", H. U. Bergmeyer, Ed., 3rd Edition, Vol. 1, pages 210–221, Verlag Chemie, Weinheim (1983) are, like the determination of glucose using glucose oxidase, based on the stoichiometric production of hydrogen peroxide. The latter can then be reacted in an oxidation, catalyzed by peroxidase, of a colorless substrate to give a colored product which is easily measured quantitatively by spectrophotometry.

Hence, large numbers of chromogenic systems suitable for this reaction catalyzed by peroxidase have been investigated and described (see Bergmeyer). Only few of them meet the requirements for the determination of peroxidase activity in enzyme immunoassays, especially in respect of the detection sensitivity. In general, a chromogenic substrate ought to permit a high rate of conversion and result in a product which has a stable color with a high molar extinction coefficient. Furthermore, substances whose manipulation does not entail any risk to health ought to be preferred. In commercial assay kits for enzyme immunoassays based on peroxidase use is made of, in particular, o-phenylenediamine (OPD) and 2,2'-azinodi-(3-ethylbenzothiazoline-6-sulfonate) (ABTS). Both OPD and ABTS are, as are most peroxidase substrates, mutagenic. One group of substrates which is often used is that of the benzidine type, one of which is tetramethylbenzidine (TMB). TMB is a safe non-mutagenic substitute for carcinogenic peroxidase substrates of the benzidine type, such as benzidine, diaminobenzidine inter alia. A large number of investigations have produced no evidence that this benzidine derivative has mutagenic properties (Tetrahedron 30, 3299 (1976); Cancer Lett. 1, 39 (1975); J. Forensic Sci. 21,816 (1976)). TMB has been employed since 1974 by various users for the determination of pseudoperoxidase activity of hemoglobin or cytochrome P 450, and it has already been used, by Liem et al., Anal. Biochem. 98, 388–393 (1979), for the detection of peroxidase activity in immune complexes by the immunoperoxidase staining technique. These authors point out, in their conclusions on page 392, that TMB has good staining properties but also that its solubility in the buffer systems usually applied is low and that TMB is subject to oxidative decomposition.

However, when TMB is used in enzyme immunoassays the low solubility of this chromogen in water proves to be very restrictive under assay conditions. Hence, in Netherlands Patent Application 8001972 of Messrs. Akzo, and in U.S. Pat. No. 4,503,143, measures increasing the solubility have been described. In both publications the improvement in solubility is achieved by use of organic solvents. Addition of dimethyl sulfoxide (1% v/v in the mixture ready for use) results in a TMB concentration of 100 mg/l, i.e. 0.42 mmol/l, according to the statements in Netherlands Patent 8001972, or of 43 mg/l, i.e. 0.18 mmol/l, in U.S. Pat. No. 4,503,143. In contrast, usually OPD and ABTS are offered to the enzyme in a molar concentration which is 50 to 100-fold higher. Alteration of the concentration of tetraalkylbenzidine in the enzyme assay shows that the saturation of peroxidase with substrate which is necessary to achieve the maximum rate of conversion is not attained with the abovementioned TMB concentrations.

Hence there has been a need to find a formulation which contains a tetraalkylbenzidine and is suitable for the determination of peroxidase but does not have the above-mentioned disadvantages. The invention relates to a formulation of this type, to its preparation and to its use.

It has been found, surprisingly, that a tetraalkylbenzidine formulation which is considerably improved in respect of detection sensitivity can be obtained by adjusting a solution which contains such a compound or one of its derivatives to a pH between 2.5 and 3.9 with an aqueous buffer which contains a suitable hydrogen peroxide concentration. Although the pH optimum for enzyme activity for customary peroxidase substrates, as well as for TMB, has been reported to be pH 5 to pH 6 (U.S. Pat. No. 4,503,143; "Methods of Enzymatic Analysis", H. U. Bergmeyer, Ed., 3rd Edition, Vol. III, pages 286–293, Verlag Chemie, Weinheim (1983)), the formulation according to the invention exhibits a detection sensitivity which is improved, at an unusually low pH, in particular in the pH range 3.1 to 3.6, compared with formulations hitherto described, as is shown in Examples 2 and 3.

The invention relates to an agent in the form of a liquid formulation for the detection and for the determination of peroxidase, containing in a predominantly aqueous solution a tetraalkylbenzidine or one of its salts, with a content of 0.6 to 4.0 mmol/l, peroxides as substrate for peroxidase, with a content of 0.5 to 50 mmol/l, and buffer substances which set up a pH in the range 2.5 to 3.9.

The agent can also contain a penicillin or one of its breakdown products produced by acid hydrolysis, as described in German Patent Application P 3,541,979.

The agent can be prepared by dissolving a solid formulation, for example a lyophilisate, granules or a tablet, where the contents of the components which are used for the liquid formulation—tetraalkylbenzidine, penicillin or its breakdown products, the peroxides and the buffer substances—are in ratios of amounts such that, on dissolution in a defined volume of predominantly aqueous solvent, the components are present in the stated concentrations. The solid formulation can additionally contain additives such as lubricants, fillers and disintegrants, for example polyethylene glycol, urea and bicarbonates.

The tetraalkylbenzidines which can be used are, in particular, those which contain one to three carbon atoms in the alkyl moiety, preferably 3,3',5,5'-tetramethylbenzidine (TMB) or its dihydrochloride. Suitable peroxides are sodium perborate, hydrogen peroxide in liquid form or as the solid urea adduct, as well as a system which generates hydrogen peroxide and is composed of D-glucose and glucose oxidase, the concentration being set at 0.5 to 10 mmol/l. Preferred buffer substances are lyotropic substances such as citrates and acetates.

The preparation of a formulation in liquid form entails the tetraalkylbenzidine being dissolved in a first acid solution, of dilute hydrochloric acid or of formic acid, with a pH of 1.5 to 2.0. The penicillin, or its breakdown products produced by acid hydrolysis, are preferably added to this solution.

A second, less acid solution is prepared by dissolving the peroxides, or by introduction thereof when a solution of hydrogen peroxide is used, in solutions of, for example, acetic acid or monosodium or monopotassium citrate whose pH can be adjusted to between 3 and 6 with sodium hydroxide.

The formulation ready for use is obtained by mixing the two solutions in a defined ratio.

The invention is illustrated in detail by the Examples which follow, but is not confined to these.

EXAMPLES

1. Preparation of a TMB substrate formulation ready for use

Stock solution 1: TMB dihydrochloride was dissolved, with stirring, at a concentration of 5 g/l, i.e. 16 mmol/l, in double-distilled water, and the pH was adjusted to 1.5 with 5-normal hydrochloric acid. To this solution was added penicillin G, with stirring, in a final concentration of 200 mg/l, i.e. 0.56 mmol/l.

Stock solution 2: 1.4 ml of glacial acetic acid, 1.5 ml of 1-normal NaOH and 250 mg, i.e. 3 mmol of $H_2O_2$, of urea-hydrogen peroxide adduct were added to 900 ml of double-distilled water. After dissolution was complete, the volume was made up to 1 l with double-distilled water.

Solution for use: One part by volume of stock solution 1 and 10 parts by volume of stock solution 2 were mixed together.

The solution for use thus prepared had a pH of 3.3. It had an optical density at 650 nm of 0.025. After addition of 5 times the volume of 0.5-normal sulfuric acid, the extinction measured at 450 nm was 0.008.

2. Kinetic assay of peroxidase activity

A conjugate of horseradish peroxidase (Boehringer Mannheim, FRG) and rabbit anti-human IgE antibodies (Behringwerke, Marburg, FRG) prepared by the method of Nakane and Kawaoi, J. Histochem. Cytochem. 22, 1084–1091 (1974) was diluted in phosphate-buffered saline (PBS) to which 10 mg/ml bovine serum albumin had been added. 20 µl of this solution was placed in a cuvette and a volume of 1 ml of the solution for use prepared as in Example 1 was added. After mixing, the change in extinction at 650 nm during the first minute was recorded. In the same way the change in extinction per minute brought about by the enzyme conjugate was recorded in a solution for use, prepared as in Netherlands Patent 8001972, Example 1 c, and comprising 99 mg/l, i.e. 0.41 mmol/l TMB in an aqueous solution of 0.99% (v/v) dimethyl sulfoxide and 8.73 g/l trisodium citrate ×1$H_2O$, which had been adjusted to pH 6.0 with phosphoric acid.

The mean obtained from a duplicate determination of the change in extinction per minute was 1.318 for the TMB solution for use according to Example 1, and the figure for the TMB solution for use according to Netherlands Patent 8001972 was 0.193.

3. Use in an enzyme immunoassay for the determination of total IgE

Polystyrene microassay plates (Nunc, Roskilde, Denmark, Cat. No. 262170) were coated by the method described by Voller et al., Bull. World Health Organ. 53. 55–65 (1976). For this purpose, 150 µl of a solution of the anti-IgE antibody indicated in Example 2 were incubated in each well in a concentration of 10 µg/ml, in the coating buffer indicated by Voller et al., at room temperature for 15–20 hours. After aspiration of the solution and washing with 1 g/l polyoxyethylene(20)sorbitan monolaurate, also called Tween®20, in PBS (PBS-Tween®), 100 µl samples of various dilutions of an IgE-containing human serum in PBS, to which 10 mg/ml bovine serum albumin had been added, were introduced into 8 wells and incubated at room temperature for 1 hour. The concentration of IgE resulting in these samples from the dilution step were 1,000, 500, 100, 25 and 10 IU/ml. After washing twice with PBS-Tween®, 100 µl of a suitable dilution of the conjugate described in Example 2, in PBS-Tween® to which 10 mg/ml bovine serum albumin had been added, were introduced into all the wells used, and incubated at room temperature for 1 hour. After once more washing twice, 100 µl of the solution for use described in Example 1 were pipetted into each of 4 of the 8 wells used for each concentration level, and incubated at room temperature for 30 minutes. 100 µl of the TMB formulation according to Netherlands Patent 8001972, as described in Example 2 were used analogously for each of the remaining 4 wells. After the incubation period had elapsed, 100 µl of a 0.5-normal $H_2SO_4$ were added, which stopped the enzyme reaction. The extinctions of the resulting colored solutions were measured using a Behring ELISA processor apparatus (Behringwerke, Marburg, FRG) and are shown in the Table.

TABLE

Extinctions in the sandwich enzyme immunoassay

| | | Mixture 1 (TMB as in Example 1) | Mixture 2 (TMB according to Netherlands Patent 8001972) |
|---|---|---|---|
| Dilutions of | 10 IU/ml | 0.077 | 0.021 |
| IgE-containing | 25 IU/ml | 0.126 | 0.038 |
| human serum | 100 IU/ml | 0.332 | 0.102 |
| (see Example 3) | 500 IU/ml | 1.018 | 0.305 |
| | 1,000 IU/ml | 1.940 | 0.612 |

1 IU = 2.3 ng IgE

We claim:

1. An agent for the detection and/or for the determination of peroxidase activity, comprising in a predominantly aqueous solution a tetraalkylbenzidine or one of its salts, a peroxide or a system generating hydrogen peroxide, and one or more buffer substances in an amount sufficient to provide a pH in the range of 2.5 to 3.9.

2. An agent as claimed in claim 1, in which the tetraalkylbenzidine contains one to three carbon atoms in the alkyl moiety.

3. An agent as claimed in claim 1, in which the tetraalkylbenzidine is 3,3',5,5'-tetramethylbenzidine.

4. An agent as claimed in claim 1, further comprising at least one of penicllin or one of its breakdown products obtained by acid hydrolysis.

5. A method of determining the presence of peroxidase activity in a material comprising:

bringing said material into contact with an agent according to claim 1 to form a mixture;

allowing said mixture to stand for a predetermined period of time; and examining said mixture for the presence of a colored product indicative of the presence of peroxidase.

6. A process for the preparation of an agent for the detection and/or for the determination of peroxidase activity, which comprises a) adding a tetraalkylbenzidine or one of its salts to a first acid solution having a pH of 1.5 to 2;

b) forming a second acid solution of peroxide and buffer substances;

c) mixing said first acid solution with said second acid solution containing peroxide and buffer substances in a ratio sufficient to provide a pH in the range of 2.5 to 3.9, wherein said agent is in a predominantly aqueous solution.

7. The process as claimed in claim 6 wherein said first acid solution is a dilute solution of hydrochloric acid or of formic acid.

8. The process as claimed in claim 6, wherein step a) also includes adding at least one of penicillin or one of its breakdown products obtained by acid hydrolysis.

* * * * *